United States Patent
Svihus

(10) Patent No.: US 11,415,446 B2
(45) Date of Patent: Aug. 16, 2022

(54) FLOW MEASURING SYSTEM

(71) Applicant: Roxar Flow Measurement AS, Stavanger (NO)

(72) Inventor: Jone Svihus, Sandnes (NO)

(73) Assignee: Roxar Flow Measurement AS, Stavanger (NO)

( * ) Notice: Subject to any disclaimer, the term of this patent is extended or adjusted under 35 U.S.C. 154(b) by 448 days.

(21) Appl. No.: 16/497,528

(22) PCT Filed: Mar. 26, 2018

(86) PCT No.: PCT/EP2018/057639
§ 371 (c)(1),
(2) Date: Sep. 25, 2019

(87) PCT Pub. No.: WO2018/178011
PCT Pub. Date: Oct. 4, 2018

(65) Prior Publication Data
US 2020/0116538 A1    Apr. 16, 2020

(30) Foreign Application Priority Data
Mar. 28, 2017   (NO) .................... 20170503

(51) Int. Cl.
*G01F 1/74* (2006.01)
*G01F 1/66* (2022.01)
*G01N 22/04* (2006.01)

(52) U.S. Cl.
CPC ............... *G01F 1/74* (2013.01); *G01F 1/66* (2013.01); *G01N 22/04* (2013.01)

(58) Field of Classification Search
CPC ..... G01F 1/74; G01F 1/66; G01F 1/36; G01F 1/34; G01F 1/05; G01F 1/02; G01F 1/00;
(Continued)

(56) References Cited

U.S. PATENT DOCUMENTS

| | | |
|---|---|---|
| 4,745,617 A | 5/1988 | Harvey |
| 5,608,665 A | 3/1997 | Wyszynski |

(Continued)

FOREIGN PATENT DOCUMENTS

| | | |
|---|---|---|
| EP | 2500699 B1 | 3/2015 |
| GB | 2376074 A | 12/2002 |

(Continued)

OTHER PUBLICATIONS

Nyfors, E.G.; "Cylindrical Microwave Resonator Sensors for Measuring Materials under Flow"; Dissertation for the degree of Doctor of Science in Technology; Helsinki University of Technology, Dept. of Electrical and Communications Engineering; Report S243; May 26, 2000; 181 pages.

(Continued)

*Primary Examiner* — Mohamed Charioui
(74) *Attorney, Agent, or Firm* — Shackelford, Bowen, McKinley & Norton, LLP

(57) ABSTRACT

The present invention relates to a measuring system for measuring dielectric properties of a multiphase fluid flow in a pipe. The system includes a microwave signal generator connected to the multiphase fluid flow for transmitting signals within a predetermined frequency range into said flow, a signal receiver adapted to receive signals within said range from said flow, and analyzing means for calculating the dielectric properties based on the transmitted and received signals. The signal generator includes: an IQ modulator being coupled to a high frequency oscillator and a low frequency synthesizer, the high frequency oscillator generating a high frequency signal $f_{LO}$, and the low frequency synthesizer is adapted to generate signals $f_{RF}$ at a number of frequencies within a chosen frequency range, said IQ-modulator being adapted to generate an output signal $IQ_{OUT}$ constituted by the combination of said signals from the (Continued)

oscillator and the synthesizer, the predetermined frequencies of the oscillator and the synthesizer being chosen based on the required output frequency range for the IQ-modulator.

10 Claims, 8 Drawing Sheets

(58) Field of Classification Search
CPC ........ G01N 22/04; G01N 22/00; G01N 33/28; G01N 33/00; E21B 47/10; E21B 47/00
See application file for complete search history.

(56) References Cited

U.S. PATENT DOCUMENTS

| | | | |
|---|---|---|---|
| 5,793,216 | A | 8/1998 | Constant |
| 5,841,288 | A * | 11/1998 | Meaney ............... A61B 5/0507 600/407 |
| 6,009,760 | A * | 1/2000 | Jakkula ................ G01F 1/712 73/861.05 |
| 6,182,504 | B1 | 2/2001 | Gaisford |
| 6,351,409 | B1 | 2/2002 | Rizzo et al. |
| 6,466,035 | B1 | 10/2002 | Nyfors et al. |
| 6,915,707 | B2 | 7/2005 | Nyfors et al. |
| 7,078,913 | B1 | 7/2006 | Pelletier |
| 8,224,588 | B2 | 7/2012 | Wee |
| 9,851,399 | B2 | 12/2017 | Finkenzeller et al. |
| 10,060,869 | B2 | 8/2018 | Nyfors |
| 10,359,372 | B2 | 7/2019 | Nyfors |
| 2003/0122067 | A1 | 7/2003 | Radtke et al. |
| 2004/0244501 | A1 | 12/2004 | Nyfors et al. |
| 2005/0188771 | A1 | 9/2005 | Lund et al. |
| 2007/0051685 | A1 | 3/2007 | Wittmer et al. |
| 2007/0224692 | A1 | 9/2007 | Agar et al. |
| 2008/0307860 | A1 | 12/2008 | Guieze et al. |
| 2009/0088985 | A1 | 4/2009 | Wee |
| 2009/0139345 | A1 | 6/2009 | Xie |
| 2009/0204346 | A1 | 8/2009 | Xie |
| 2010/0145636 | A1 * | 6/2010 | Nyfors .................. G01F 1/86 702/49 |
| 2010/0148804 | A1 | 6/2010 | Jakoby et al. |
| 2011/0061475 | A1 | 3/2011 | Guieze et al. |
| 2011/0095772 | A1 | 4/2011 | Sidhu et al. |
| 2011/0118990 | A1 | 5/2011 | Sidhu et al. |
| 2011/0138928 | A1 * | 6/2011 | Xie ..................... G01F 1/44 73/861.63 |
| 2012/0006430 | A1 | 1/2012 | Gentile et al. |
| 2013/0009646 | A1 | 1/2013 | Simon et al. |
| 2014/0102181 | A1 | 4/2014 | Mohajer |
| 2014/0216936 | A1 | 8/2014 | Hughes et al. |
| 2017/0038311 | A1 | 2/2017 | Conrad |

FOREIGN PATENT DOCUMENTS

| | | |
|---|---|---|
| JP | H01155246 A | 6/1989 |
| JP | 2002005971 A | 1/2002 |
| NO | 308922 B1 | 11/2000 |
| NO | 315584 B1 | 9/2003 |
| RU | 2192646 C1 | 11/2002 |
| WO | WO-99063331 A2 | 12/1999 |
| WO | WO-03012413 A2 | 2/2003 |
| WO | WO-03034051 A1 | 4/2003 |
| WO | WO-2005057142 A1 | 6/2005 |
| WO | WO-2006019311 A1 | 2/2006 |
| WO | WO-2007018434 A1 | 2/2007 |
| WO | WO-2007089156 A1 | 8/2007 |
| WO | WO-2007129901 A1 | 11/2007 |
| WO | WO-2008085065 A1 | 7/2008 |
| WO | WO-2010115883 A1 | 10/2010 |
| WO | WO-2013084183 A2 | 6/2013 |
| WO | WO-2013181173 A1 | 12/2013 |
| WO | WO-2014122093 A1 | 8/2014 |
| WO | WO-2016/077011 A1 | 5/2016 |
| WO | WO-2016169847 A1 | 10/2016 |

OTHER PUBLICATIONS

Wylie, S.R., et al.; "RF sensor for multiphase flow measurement through an oil pipeline"; Measurement Science and Technology, vol. 17, No. 8; Jul. 13, 2006; pp. 2141-2149.

Martin, Hazel, International Search Report prepared for PCT/EP2018/057639, dated Jul. 10, 2018, 4 pages.

Nguyen, Tuan A., et al.; "Instantaneous high-resolution multiple-frequency measurement system based on frequency-to-time mapping technique"; Optics Letters, Optical Society of America, vol. 39, No. 8; 15; Apr. 2014; pp. 2419-2422.

Xie, Cheng-gang; "Measurement of Multiphase Flow Water Fraction and Water-Cut"; AIP Conference Proceedings, vol. 914; Jun. 8, 2007; pp. 232-239.

Masse, Cecile; "Wideband Direct Conversion for Multi-Carrier Base Stations"; Proceedings from the 2nd European Wireless Technology Conference, EuWIT, Rome; Sep. 28-29, 2009; pp. 210-213.

* cited by examiner

FLOW MEASURING SYSTEM

TECHNICAL FIELD OF THE INVENTION

The present invention relates to a measuring system for measuring dielectric properties of a multiphase fluid flow in a pipe. The system includes a microwave signal generator for transmitting signals within a predetermined frequency range into said flow and a signal receiver adapted to receive signals from said flow and analyzing means for calculating the dielectric properties.

BACKGROUND

There are many types of microwave sensors in use in meters for various kinds of applications. In a meter there is always an electronics module connected to the sensor for measuring the properties of the sensor. The present invention relates to the use of resonator sensors within or close to the microwave range. The use of microwave resonators for measuring fluid characteristics in flow meters is well known in the oil and gas industry, for example as discussed in WO2014/122093 and WO2016/169847 providing salinity measurements in a fluid flow.

As an example a resonator sensor displays a resonance peak, when the insertion loss is measured. The peak has two main properties, which are the primary measurement results, the resonant frequency and the Q-factor, i.e. at which frequency the peak appears and how wide or sharp it is. The electronics needs to be able to find the peak within a given frequency range, which might be quite broad, e.g. an octave or more. In on-line applications the peak might in addition change position and shape quite fast. Then the measurement must be performed so fast that it will in practice represent an instantaneous snapshot of the peak. It is therefore an object of the present invention to provide a sufficiently fast measurement. This is obtained by utilizing a system as described in the accompanying claims.

The most accurate method of measuring a resonance peak is to sample the insertion loss at a number of frequencies, and perform a curve-fit to find the resonant frequency and Q-factor. But if the frequencies are sampled one by one, the movement of the peak during the sampling process creates an error especially in the Q-factor. The sampling process must be fast compared to the dynamics in the resonance peak. Another alternative is to use a multi-tone signal and sample all frequencies simultaneously, as enabled by one embodiment of this invention.

Another type of microwave sensor is a transmission sensor. Then a signal is transmitted from one small antenna, often called a probe, to another one. On the path the signal passes through the medium to be measured and both the phase shift and the attenuation of the signal are affected by the properties of the medium. Also in this case the properties to be measured may vary fast in on-line applications. In addition, it is often of interest to measure at several, often widely separated, frequencies to gather information on frequency-dependent properties. The phase shift and/or the attenuation may therefore be measured at more than one frequency. Also in this case it may be an advantage to sample all the measurement frequencies simultaneously, or within a very short time interval, to capture data at all the frequencies corresponding to the same measurement situation. E.g. if the sensor is used for measuring a flow of oil, water and gas in a pipe, and the flow moves so fast that while the measurement at one frequency is performed when a gas slug passes the sensor, the measurement at another frequency is performed when there is substantially more liquid at the sensor, the two measurements correspond to different situations and are not directly comparable. In such cases averaging over a much longer time is needed to get useful results. If all the measurement frequencies can be sampled simultaneously, or almost simultaneously, as enabled by one embodiment of the invention, this improves the quality of the results, and shortens the time to reach a high accuracy for the measured and derived properties, which may be e.g. the salinity of the water component, the GVF (Gas Void Fraction), or the water to oil ratio in a flow of oil, water and gas.

SUMMARY

Therefore one aspect of the present invention is aimed at detecting the dielectric properties of a flow by using an IQ converter to combine a high frequency range signal from a high frequency generator such as a PLL with an easy to manipulate lower frequency signal from a frequency synthesizer such as a DAC (or DDS) or similar electronic circuit for generating any of a range of frequencies from a single fixed timebase or oscillator, to generate an easy to manipulate, high frequency range signal. The high frequency signal is coming from the PLL (up to several GHz for the use in multiphase flow meters) but as it is difficult to manipulate this signal a lower frequency signal from a DAC is provided manipulating the higher frequency signal using a IQ modulator.

BRIEF DESCRIPTION OF THE DRAWINGS

The invention will be described more in detail below with reference to the accompanying drawings illustrating the invention by way of examples.

DETAILED DESCRIPTION

Figure 1A:
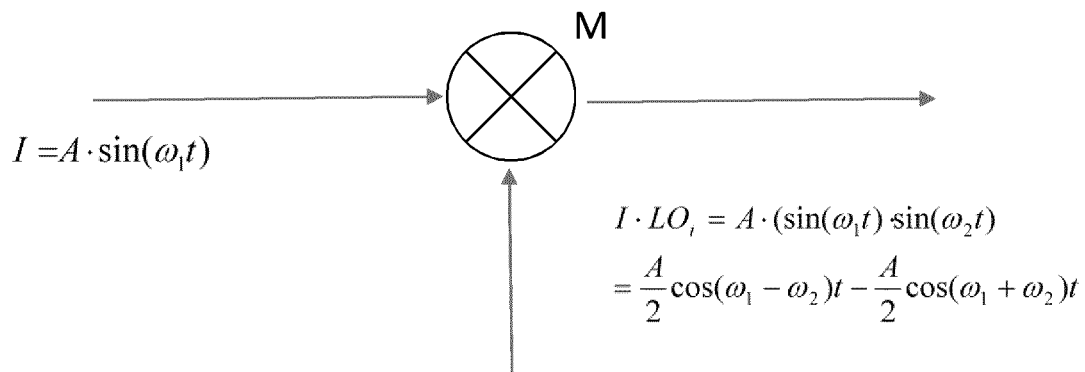
FIG. 1a-h illustrates the details of IQ-modulators used according to the invention.

As illustrated in FIGS. 1a-h an IQ modulator is based on mixing signals. FIG. 1a shows a standard frequency multiplier M where two sinus signals I, LOi mixed together will form two new signals I·LOi with respectively the sum of and the difference between the two signals given by:

$$I \cdot LO_i = A \cdot (\sin(\omega_1 t) \cdot \sin(\omega_2 t))$$

$$= \frac{A}{2}\cos(\omega_1 - \omega_2)t - \frac{A}{2}\cos(\omega_1 + \omega_2)t$$

Figure 1B:
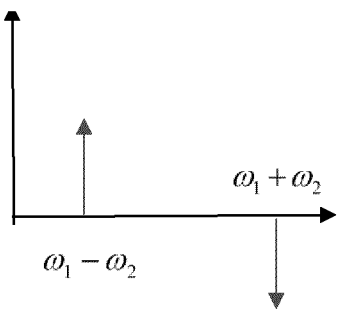

In FIG. 1b the amplitude vs frequency is illustrated and as can be seen in the spectrum the sum of the frequencies, $\omega_1+\omega_2$, has negative amplitude while the difference, $\omega_1-\omega_2$, has a positive amplitude.

Figure 1C:
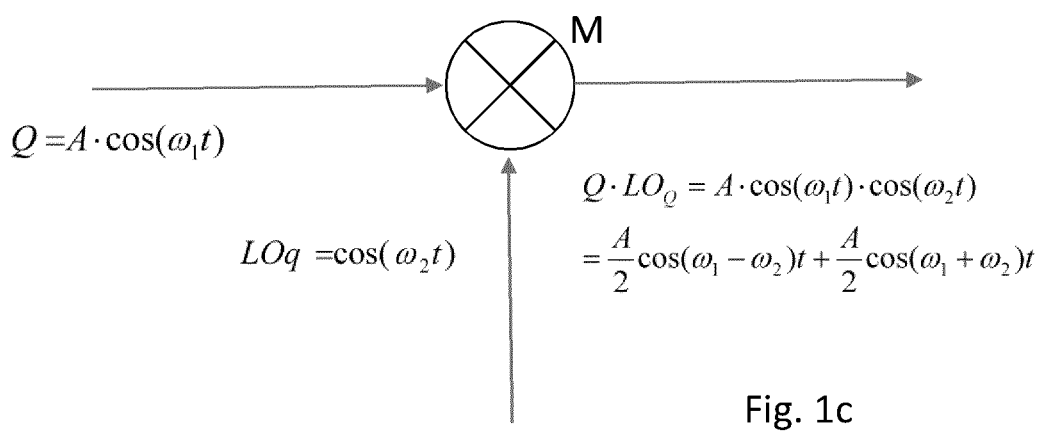
Figure 1D:
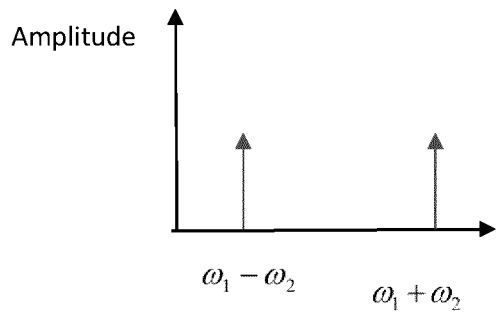

If both signals I and LOi are shifted 90 degrees (sin+90 degrees is cos), it changes to the situation as is shown in FIGS. 1c and 1d, where Q and $LO_q$ are mixed shifting the sum of the frequencies, $\omega_1+\omega_2$, to be positive. Thus as illustrated in FIG. 1d.

$$Q \cdot LO_Q = A \cdot \cos(\omega_1 t) \cdot \cos(\omega_2 t)$$
$$= \frac{A}{2}\cos(\omega_1 - \omega_2)t + \frac{A}{2}\cos(\omega_1 + \omega_2)t$$

Since the goal of an IQ modulator is to mix two signals and achieve a signal with a single frequency, the above circuits are combined and a summing device S is added. Both multipliers M and the summer S are basic electronic devices that will not be described here.

Figure 1E:
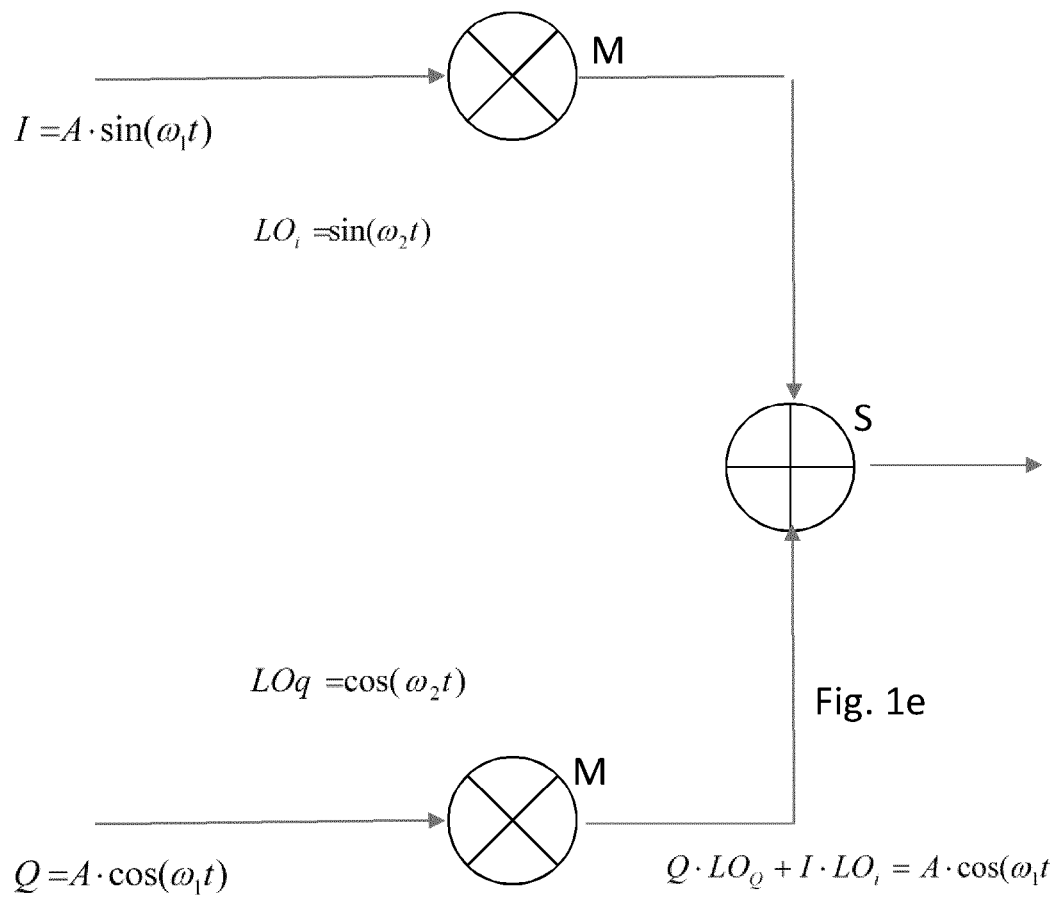

FIG. 1e illustrates a basic sketch for a mixer where the I and Q signals are mixed with LOi and $LO_q$ signals, respectively, and the outputs from these mixers are added to provide the sum $Q \cdot LO_q + I \cdot LO_i$. The result of this operation may be expressed as $$Q \cdot LO_Q + I \cdot LO_i = A \cdot \cos(\omega_1 t) \cdot \cos(\omega_2 t) + A \cdot \sin(\omega_1 t) \cdot \sin(\omega_2 t)$$
$$= \frac{A}{2}\cos(\omega_1 - \omega_2)t + \frac{A}{2}\cos(\omega_1 + \omega_2)t +$$
$$\frac{A}{2}\cos(\omega_1 - \omega_2)t - \frac{A}{2}\cos(\omega_1 + \omega_2)t$$
$$= A \cdot \cos(\omega_1 - \omega_2)t$$

Figure 1F:
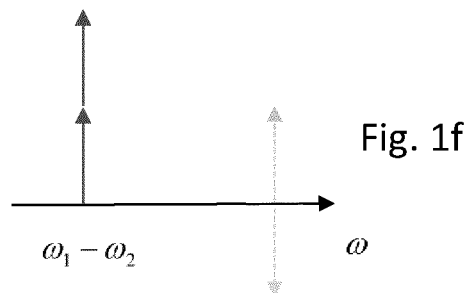

And can be seen both vector representation in FIG. 1f. One of the frequency components is cancelled and the output signal consist of a single frequency $\omega_1 - \omega_2$ equal to the difference between the frequencies of the input signals.

This principle is widely used in for instance communication systems, in most systems the I and Q signals are low frequency signals and the LOi and LOq are at a much higher frequency. Also the I and Q signals are complex signals (multiphase and multi frequency) and the LOi and LOq are single frequency carrier signals. If the I and Q have several frequencies, each of the frequencies needs to be shifted 90 degrees. Since the I and Q signals in most applications are complex signals with different phases and frequencies they are generated with DAC's combined with a processing unit (for instance a DSP, Digital Signal Processor). Provided that the DAC's are synchronized (using a single clock) a processor can calculate both the I signal and the corresponding 90 degree shifted Q signal for all the different frequencies in the I signal.

Figure 1G:
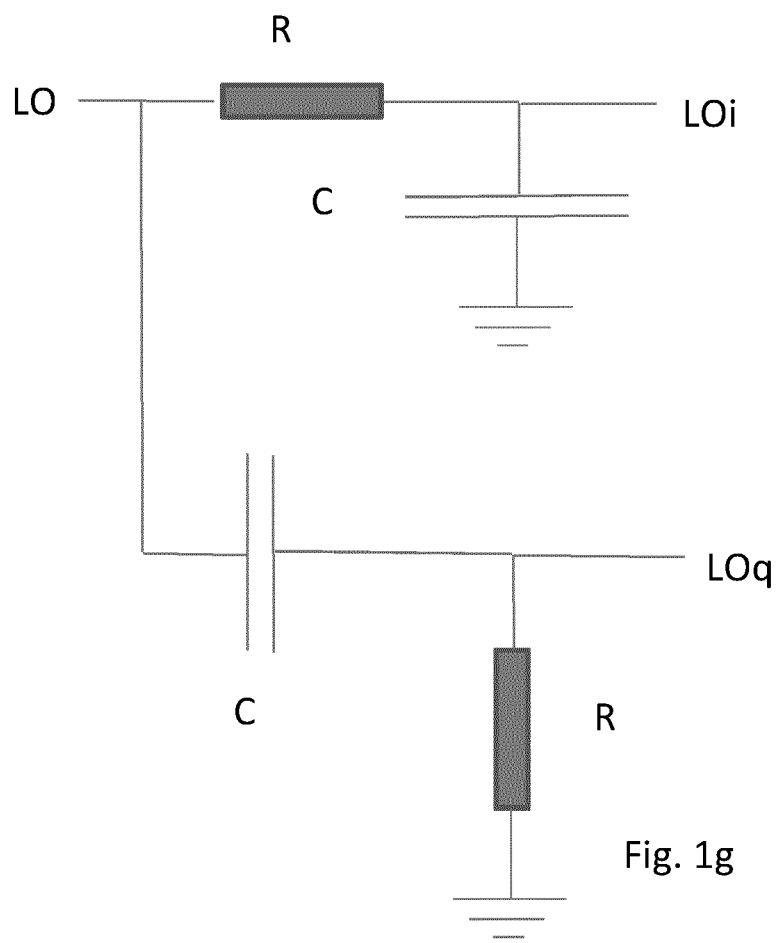

The generation of the LOi and LOq signals (to be mixed with the I and Q signals respectively) from one LO signal may be performed in different ways, where FIG. 1g illustrates the use of an RC filter. If the two R and C's are matched the two signal will have exactly 90 degrees phase difference, the amplitude will however differ which can be restored by running both the LOi and LOq through a comparator and generate a square wave with a set amplitude.

Figure 1H:
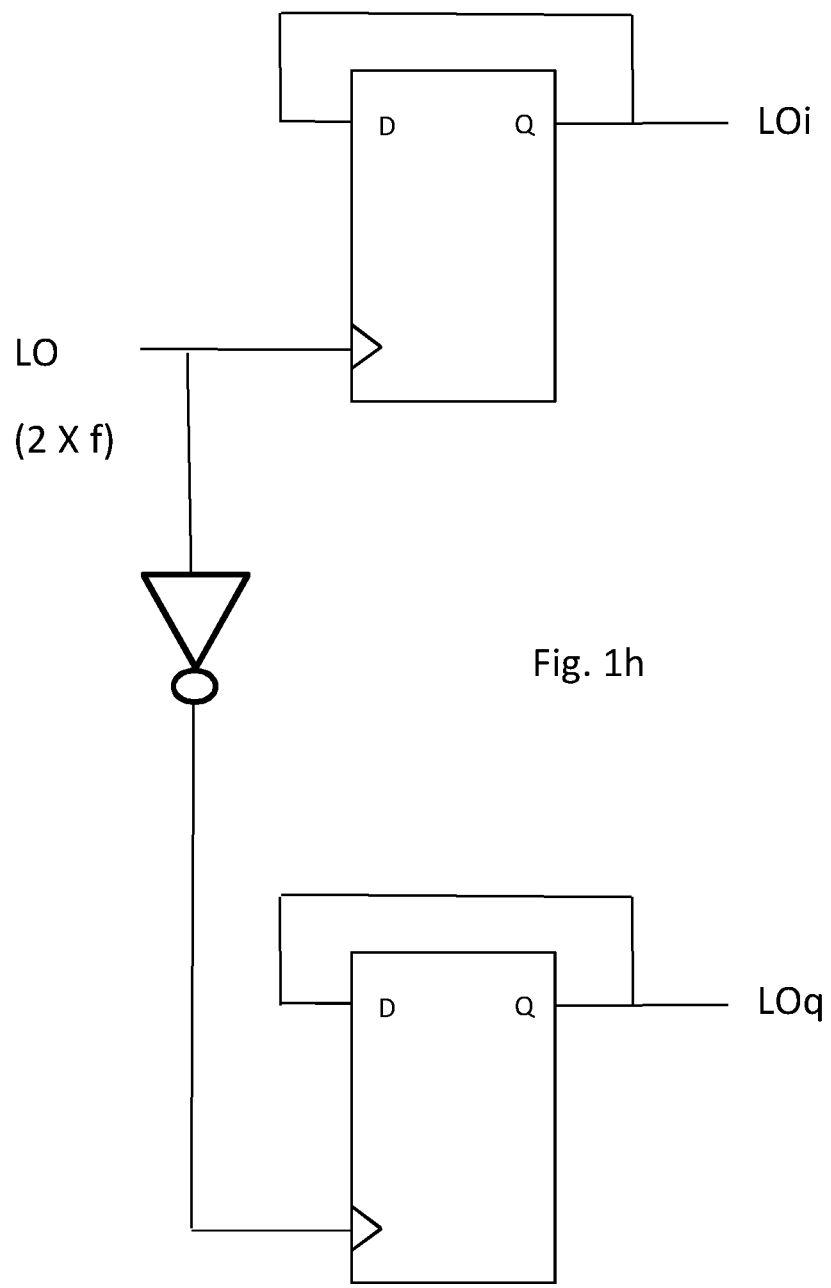

FIG. 1h illustrates an alternative way to generating the LOi and LOq signals using a frequency divider. Starting with a frequency twice the desired frequency f and inverting it will result in a 90 degrees phase shift when both signal are used to trigger a frequency divider. In most applications the starting point is a differential LO signal and two identical frequency dividers, cross connecting the positive and negative part of the LO signal on the two frequency dividers enables a precise 90 degree phase shift.

Figure 2A:
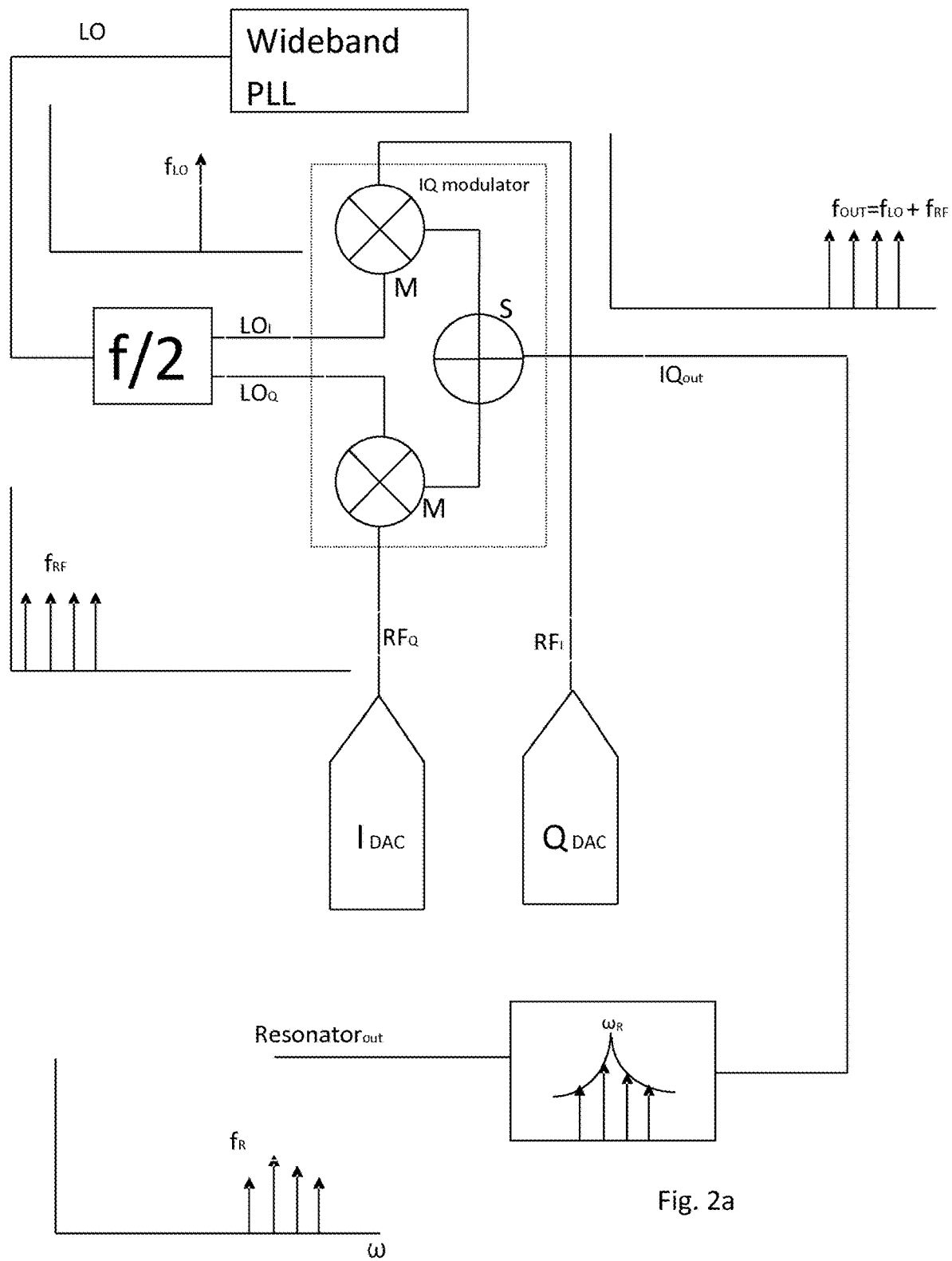
FIG. 2a illustrates a first embodiment of the invention.

FIG. 2a shows an IQ modulator setup based on the discussion related to FIGS. 1e and 1h. The illustrated embodiment includes a PLL, preferably capable of covering a wide frequency range, an IQ modulator and two DAC's (Digital to Analog Converter) $I_{DAC}$, $Q_{DAC}$. In the shown embodiment the signal from the PLL is divided as illustrated in FIG. 1h in order to produce the two LO inputs, LOi, LOq to the IQ modulator.

The PLL in FIG. 2a may provide a frequency within a wide range from a few megahertz up to several Gigahertz, but the frequency cannot change instantly (typically 1 µs to settle on a new frequency) and the PLL cannot be used to generate multi-tunes. The DAC's, however, are generating a lower frequency signal typically from a few hundred kilohertz up to some 10's of Megahertz (limited by the clock frequency of the ADC's in the IQ demodulator, for example 30 MHz).

The advantage of using the two DAC's is that they can generate several tunes $f_{RF}$ at the same time and even white noise if needed, provided that the DAC's are clocked by a frequency much higher than the frequency of the output signal, for example 300 MHz. Note that a DDS (Direct Digital Synthesis) is also considered to be a DAC (a DDS is a DAC with a dedicated control system).

In FIG. 2a the output from the DAC's is illustrated as a signal with number of distinct frequency components $f_{RF}$ at a relatively low frequency compared to the PLL signal. The IQ modulator needs both the I and Q version of both the signal from the PLL($LO_I$, $LO_Q$) and from the DAC's ($RF_I$, $RF_Q$) and provides signal $IQ_{OUT}$ at a corresponding number of output frequencies with known amplitudes that are applied to the microwave sensor, in this example illustrated as a resonator. This is illustrated with the $f_R$, a multitone signal at a high frequency. This process is usually referred to as an IQ modulation or a Single Side Band mixing (SSB).

According to the invention, when tracking a resonator, the PLL is in this embodiment is aiming to find the resonance frequency $\omega_R$ of the resonator in a certain range by applying signals at chosen frequencies within the range expected to have a resonance peak. Using an IQ modulator generating the signals and then measuring the amplitude and the phase of the signals from the resonator the information can be used to determine the frequency of the resonance peak without sweeping over the frequency range.

This may be used to provide an instant measurement to determine the peak and possibly the Q-factor of the resonance $\omega_R$ by means of curve fitting the information based on the amplitudes of the multiple frequency points $f_R$ illustrated in FIG. 2a as the Resonator$_{out}$. In the drawing four frequencies are used but other numbers may be used depending on the required accuracy in the calculated resonance frequency and the characteristics of the DACs and receiver system.

As an alternative to the plurality of fixed frequencies a fast sweeping over a limited frequency range (up to a few MHz) may be performed using the DAC's for providing the varying frequency, while the slower PLL may provide a constant base frequency. This way it is possible to make sure that one of the frequencies moves into the resonance frequency, thus being detected at the receiver means.

Using the limited frequency sweep the responsiveness of the system may be increased, but will require an increase in the processing power and advantageously increased amplification of the measured signals since:

$$P_{total} = \sqrt{P_{f1} + P_{f2} + P_{f3} \dots}$$

There are 4 different frequencies in FIG. 2a, in reality it is also possible to use more, such as 20, 100 or even white noise, depending on the device being measured. Depending on how well known the shape of the resonance peak is it may also be possible to use three frequencies.

The f/2 part in the illustrated example is used to divide the frequency in order to generate two signals with identical frequency and these signals needs to be exactly 90 degrees phase shifted to suppress the mirror signal (if we are generating f1+f2 the mirror signal has f1−f2). If the LO signal goes to 2 different circuits, one divides the frequency in 2 (a D flip-flop for instance), the other inverts the signal and then divides the frequency, then the result is 2 signals 90 degrees phase shifted, as is described in FIG. 1h. The alternative is an RC network as illustrated in FIG. 1g, but this is less precise.

As an alternative to DAC's a Digital Direct Synthesis (DDS) with I and Q output exists, being able to be programmed to produce frequency patterns that could be used directly.

Figure 3A:
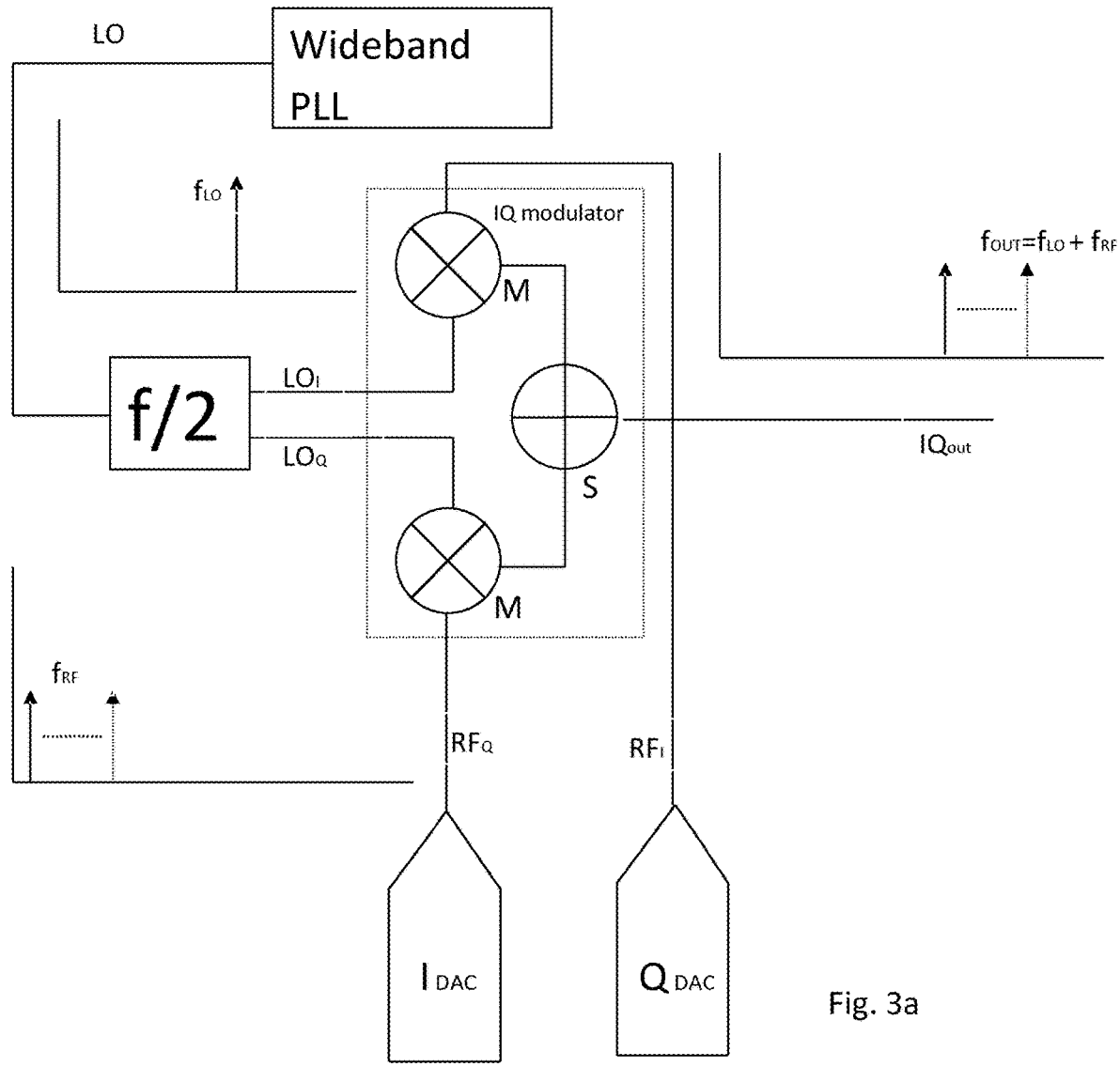
FIG. 3a, b illustrates and alternative embodiment of the invention.

In FIG. 3a an embodiment is shown using the IQ modulator for rapid scanning of a large frequency range. A wide band PLL is generally slow, after a frequency shift the PLL can take typically 1 µs to stabilize in the new frequency setting. Rapid scanning of a wide frequency range with high resolution is therefore a slow process with a PLL. A DAC on the other hand (or a DDS which is practically the same) changes frequency instantaneously and this allows for a rapid, high resolution scan. The disadvantage of using a DAC is that the clock frequency needs to be many times higher than the output frequency in order to avoid dominant spurious frequencies. This limits the max frequency in these components and makes it hard to use them in the GHz range.

This embodiment of the invention allows for both rapid, high resolution scanning and high frequency output signals with low spurious levels. The PLL produces a high frequency signal, (GHz range) and this is added with the lower frequency signal from the 2 DAC's (MHz range). The 2 DAC's produces identical signals with a 90 degrees phase between them (I and Q), this allows for the frequency of the signal from the PLL ($f_{LO}$) and the frequency of the signals from the DAC's ($f_{RF}$) to be added producing a signal with a frequency equal to the sum of frequency of $f_{RF}$ and $f_{LO}$.

Figure 3B:
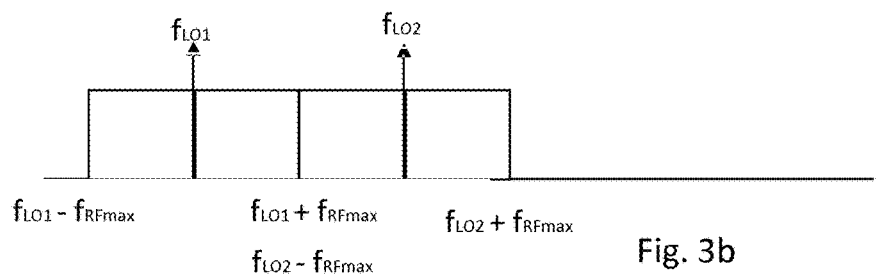

By using the DAC's to scan between 0 and the max DAC frequency $f_{RF\ max}$ we can perform a rapid scan around the PLL frequency $f_{LO}$. (changing the order of the I and Q signal from the DAC will cause the frequency to be subtracted instead of added to the PLL frequency). After this operation we will have scanned (rapidly with high resolution) a band around the PLL frequency. To continue the scanning the PLL frequency may be increases with $2 \times f_{RF\ max}$. As illustrated in FIG. 3b a scan is performed from $f_{LO1}-f_{RFmax}$ to $f_{LO1}+f_{RFmax}$ by changing the frequency from the DAC but without changing the PLL frequency ($f_{LO1}$), after the scan from $f_{LO1}-f_{RFmax}$ to $f_{LO1}+f_{RFmax}$ has been completed the PLL frequency is increased with $2 \times f_{RF\ max}$ to $f_{LO2}$, then the band from $f_{LO2}-f_{RFmax}$ to $f_{LO2}+f_{RFmax}$ is scanned so that all intermediate frequencies between $f_{LO1}-f_{RFmax}$ and $f_{LO2}+f_{RFmax}$ are covered.

The advantages with this system are as follows. Few and large steps may be provided by the PLL, and therefore slow settling of the PLL will have less impact on the scanning speed. The DAC's (or DDS) may be operated with a high ratio between the clock signal and the RF signal, securing low spurious levels. The PLL signal can be used in the demodulator ensuring that there is a frequency difference between the signal used for measurement and the reference signal this will help avoiding leakage.

Figure 2B:
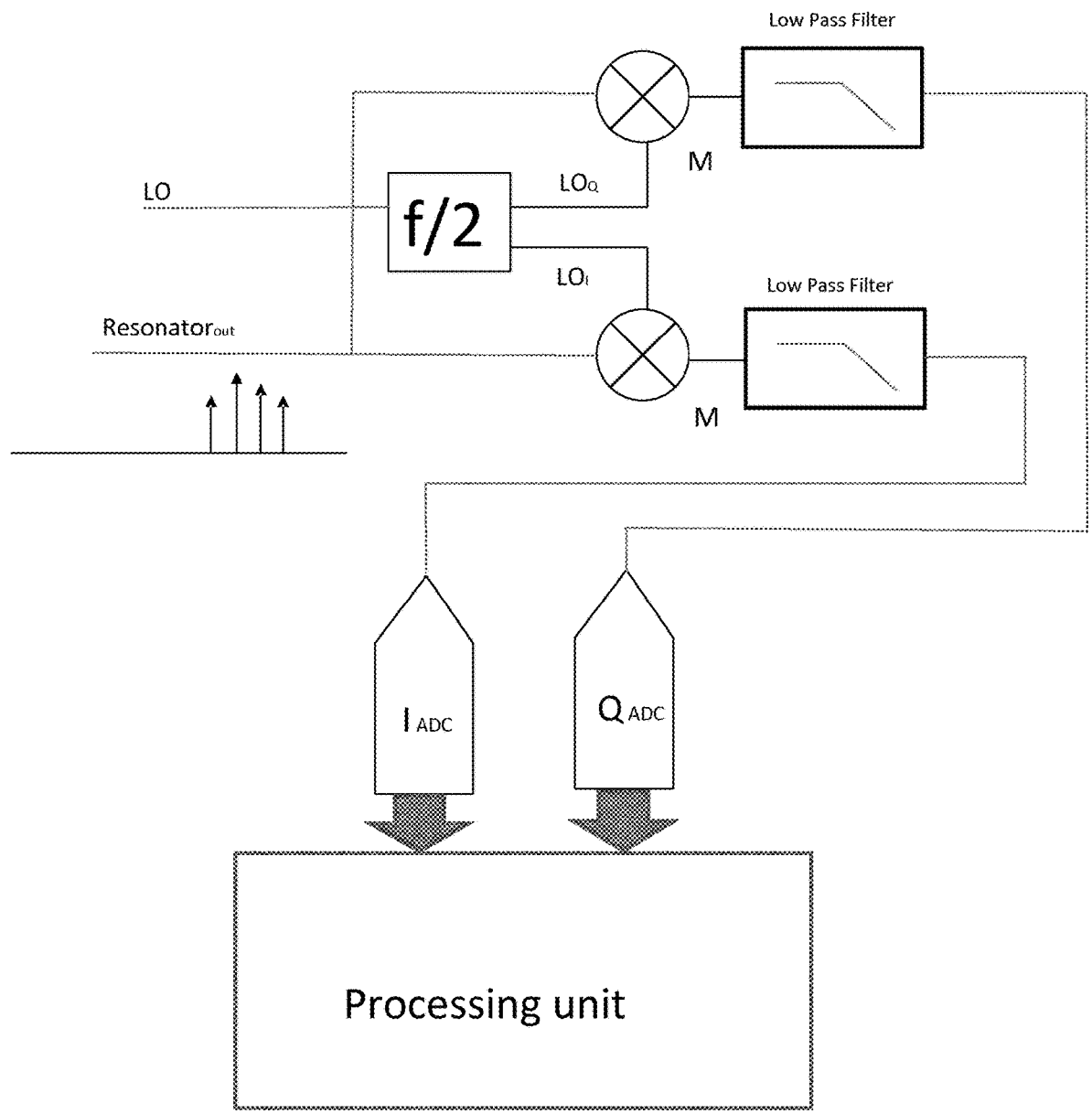
FIG. 2b illustrates an example of an IQ de-modulator
Figure 4:
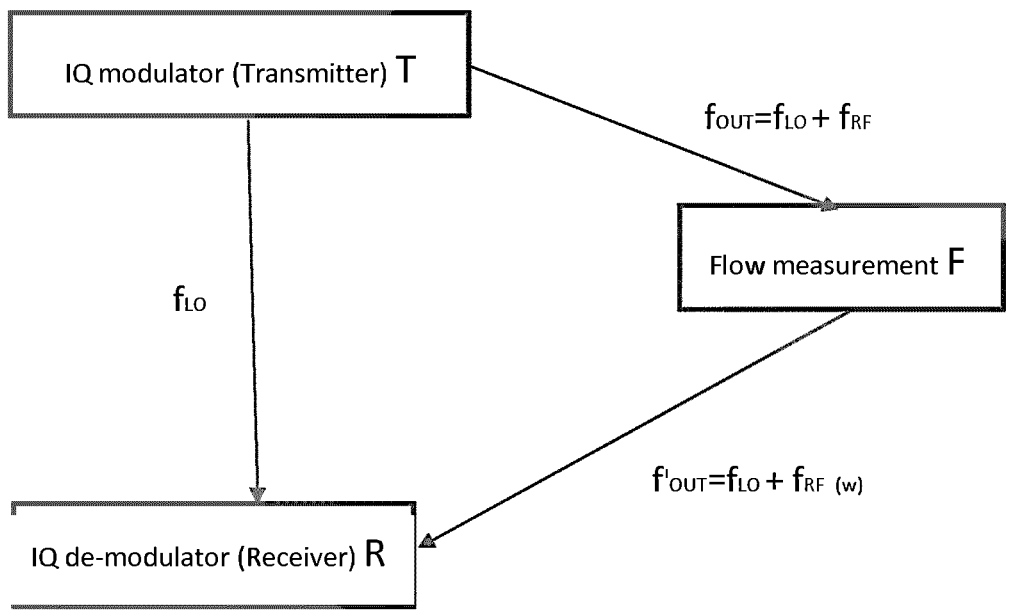
FIG. 4 Illustrates a measuring system including the resonator to be monitored.

In FIG. 4 an implementation of the system is illustrated. The output from the IQ modulator $f_{OUT}=F_{Lo}+f_{RF}$ is transmitted to the resonator in the flow measuring system, e.g. of the types discussed in WO2014/122093 and WO2016/169847. The output from the resonator $f'_{OUT}=f_{Lo}+f_{RF(W)}$ is transmitted to an IQ demodulator of any per se known type. An example of an IQ de-modulator is illustrated in FIG. 2b. FIG. 2a shows a IQ modulator and a resonator, FIG. 2b illustrates how the signals coming out of the resonator can be demodulated. The IQ modulator up converts the signals to the frequency needed to analyze the resonator, the IQ demodulator down converts the signals to a frequency that within the range of an ADC. The I and Q ADC's provides information containing the phase and gain of the frequencies in the signal to a processing unit that can extract this. The IQ demodulator also receives the LO signal as a reference from the IQ modulator. As the frequency of the attenuated output signal from the resonator is different from the reference signal leakage between the reference and measuring signals is avoided.

To summarize the invention relates to a measuring system for measuring dielectric properties of a multiphase fluid flow in a pipe. The system including a microwave signal generator connected to the multiphase fluid flow for transmitting signals within a predetermined frequency range into said flow through an antenna or similar. In a similar way the signal receiver may include an antenna or similar and is adapted to receive signals within said range from said flow. It also includes analyzing means for calculating the dielectric properties based on the transmitted and received signals. It should be noted that the "microwave range" in this case is meant in a broad sense covering the frequency range in or close to the usual definition, as ranges needed for measuring the dielectric characteristics may vary. Also, the phrase multiphase fluid may also include wet gas.

The signal generator unit used according to the invention for generating high frequency signals for a flow meter including a high frequency oscillator such as a Phase Locked Loop (PLL) oscillator generating a first, high frequency signal $f_{LO}$, the output of the oscillator being connected to the first I and Q inputs of an IQ modulator. The system also comprises a low frequency oscillators constituted by a frequency synthesizer adapted to generating signals in several frequencies sequentially of simultaneously within a chosen frequency range $f_{RF}$, preferably within a short time window so as to sample a measurement in the frequency range within the same flow volume, the duration of the time window depending on the known flow velocity. The output signal frequency $f_{RF}$ of the frequency synthesizer is significantly lower than the high frequency signal $f_{LO}$, each being coupled the I and Q modulator inputs of the IQ modulator. The IQ-modulator thus generates output signals constituted by the mix of the input signals, i.e. a sum or difference between the high frequency signals $f_{LO}$ and the low frequency signal $f_{RF}$ at the modulator input, wherein the output range of the IQ modulator is defined by a range above and below the frequency of the oscillator.

The system according to the invention may therefore provide a rapid frequency scan over a predetermined frequency range where the speed of the scan is driven by the frequency synthesizer and the carrier frequency is given by the oscillator. The scanning may alternatively be provided in two frequency ranges simultaneously as the frequency synthesizer may be capable of operating at more than one frequency at the same time. Also it is possible to extend the scanning range by changing the first, oscillator frequency The pipe containing the flow may constitute or include a resonator within the frequency range. As an example frequency synthesizer may be adapted to emit signals at at least three fixed frequencies having known amplitudes, the receiver means being adapted to analyze the amplitudes of the received signal at each frequency and finding resonance frequency of the resonator by interpolating the amplitude curve between said frequencies. Alternatively the synthesisor may be adapted to emit a rapid frequency scan having known amplitude and the analyzing means may analyse the signal so as to find resonance frequency. I both cases the Q-factor may also be calculated.

When used in a microwave resonator measuring system the generator is adapted to emit the output signal into a resonator for finding the resonance frequency of the resonator. In a preferred embodiment the output of said IQ modulator may include at least four different frequencies. The system also comprising receiver means for measuring the amplitude of the signals at said output frequencies and analyzing means for calculating the resonance frequency and preferably also the Q factor based on the amplitude and frequencies of the received signals.

Alternatively, the IQ modulator output signal including a signal having a varying frequency, the system including a receiver means and an analyzing means for analyzing the amplitudes of the received signal and finding the resonance frequency and preferably also the Q-factor of the resonator.

The system according to the invention may also be adapted to emit the output of the signal generator into an antenna in a transmission sensor system, measuring the received signal at another antenna, the IQ modulator output signal including a signal having a varying frequency, the system including a receiver means and an analyzing means for analyzing e.g. the phase shift and attenuation between the two antennas. The properties of the medium between the antennas can thereby be measured over a broad frequency range within a very short time window.

What is claimed is:

1. A measuring system for measuring dielectric properties of a multiphase fluid flow in a pipe, the measuring system comprising:
   a microwave signal generator connected to a microwave sensor constituted by a resonator in the multiphase fluid flow for transmitting signals $f_{OUT}$ within a predetermined frequency range into the flow, the pipe constituting or including the resonator within the frequency range, signal receiver adapted to receive signals within the range from the resonator in the flow, and analyzing means for calculating the dielectric properties based on the transmitted and received signals;
   wherein the signal generator comprises an IQ modulator coupled to a high frequency oscillator and a low frequency synthesizer;
   wherein the high frequency oscillator generates a high frequency signal $f_{LO}$ in the MHz to GHz range;
   wherein the low frequency synthesizer is adapted to generate signals $f_{RF}$ at a number of frequencies within a chosen frequency range lower than the high frequency signal, the chosen frequency range being in the kHz to MHz range;
   wherein the IQ-modulator is adapted to generate an output signal $IQ_{OUT}$ constituted by the combination of the signals from the oscillator and the synthesizer, the predetermined frequencies of the oscillator and the synthesizer being chosen based on the required output frequency range for the IQ-modulator;
   wherein the signal transmitted from the IQ modulator into the resonator in the flow is $f_{OUT}=f_{LO}+f_{RF}$; and
   wherein the receiver includes an IQ demodulator receiving an output signal $f'_{OUT}=f_{LO}+f_{RF(w)}$ from the resonator in the flow, the IQ demodulator also being connected to the IQ modulator for receiving the high frequency signal $f_{LO}$, the demodulator converting the signal to a frequency in the range of an ADC so as to provide I and Q signals to the processing unit to extract the information about the flow.

2. The system according to claim 1, wherein the frequency synthesizer simultaneously emits at least two different frequency signals, the output of the IQ modulator thus being constituted by a mix of the high frequency signal and the signals from the second oscillator.

3. The system according to claim 1, wherein the frequency synthesizer emits a sequence of different frequencies within the range.

4. The system according to claim 3, wherein the sequence constitutes a frequency scan over a predetermined frequency range.

5. The system according to claim 1, wherein the frequency synthesizer is a DAC adapted to control the output frequency and amplitude.

6. The system according to claim 1, wherein the pipe constitutes a resonator in the frequency range, where the frequency synthesizer is adapted to emit signals at at least three fixed frequencies having known amplitudes, the receiver means being adapted to analyze the amplitudes of the received signal at each frequency and finding resonance frequency of the resonator by interpolating the amplitude curve between the frequencies, the analyzing means being adapted to calculate the dielectric properties from the resonance frequency.

7. The system according to claim 1, wherein the pipe constitutes a resonator in the frequency range, where the frequency synthesizer is adapted to emit a rapid frequency scan having known amplitude, the receiver means being adapted to analyze the received signal so as to find resonance frequency of the resonator, the analyzing means being adapted to calculate the dielectric properties from the resonance frequency.

8. The system according to claim 6, wherein a Q-factor of the resonance peak at the resonance frequency is calculated.

9. The system according to claim 7, wherein the oscillator is adapted to change first frequency, thus allowing to change the scanning range of the signal generator.

10. The system according to claim 1, wherein the receiver means is adapted to calculate the transmission time and attenuation of the transmitted signal through the flow, the analyzing means being adapted to calculate the dielectric properties from the transmission time and attenuation.

* * * * *